United States Patent [19]

Piron

[11] Patent Number: 4,735,673
[45] Date of Patent: Apr. 5, 1988

[54] MACHINE FOR FASTENING STRETCHED PIECES OF ELASTIC BAND TRAVERSELY TO A CONTINUOUSLY MOVING SHEET

[75] Inventor: Jean-Paul Piron, Thoissey, France

[73] Assignee: Colgate-Palmolive Company, New York, N.Y.

[21] Appl. No.: 16,684

[22] Filed: Feb. 19, 1987

[51] Int. Cl.⁴ .............................................. B32B 31/08
[52] U.S. Cl. .................... 156/496; 156/164; 156/229; 156/556; 156/578
[58] Field of Search ............ 156/163, 164, 229, 495, 156/486, 519, 555, 556, 578, 291; 29/125, 130, 116 R

[56] References Cited

U.S. PATENT DOCUMENTS

| | | | |
|---|---|---|---|
| 2,927,349 | 3/1960 | Maurer | 29/116 R |
| 3,964,658 | 6/1976 | Edwards | 29/125 |
| 4,284,454 | 8/1981 | Joa | 156/229 |
| 4,285,747 | 8/1981 | Rega | 156/164 |
| 4,297,157 | 10/1981 | Van Vliet | 156/164 |
| 4,364,787 | 12/1982 | Radzins | 156/495 |
| 4,523,969 | 6/1985 | Spencer | 156/164 |
| 4,543,154 | 9/1985 | Reiter | 156/496 |
| 4,642,151 | 2/1987 | Coenen | 156/164 |

Primary Examiner—Jerome Massie
Attorney, Agent, or Firm—H. S. Sylvester; N. Blumenkopf; M. M. Grill

[57] ABSTRACT

This machine is intended for bonding stretched pieces of elastic band to a moving sheet so that these pieces extend transversely relative to the direction of movement of this sheet.

The pieces are transferred from a cutting station to a stretching station by means of a transfer station.

The stretching station comprises several pairs of grippers distributed around an axis about which they are driven in rotation. The grippers of one and the same pair are arranged axially opposite one another and are designed to be successively moved away from, and close to, one another so that, during their rotation, they grip the lateral ends of the pieces subsequently stretching the latter by moving axially away from one another. Once stretched, the pieces are bonded to the sheet entrained about a drum at the moment when the grippers pass opposite this sheet.

The invention is used for the production of a composite sheet intended for providing diapers.

14 Claims, 13 Drawing Sheets

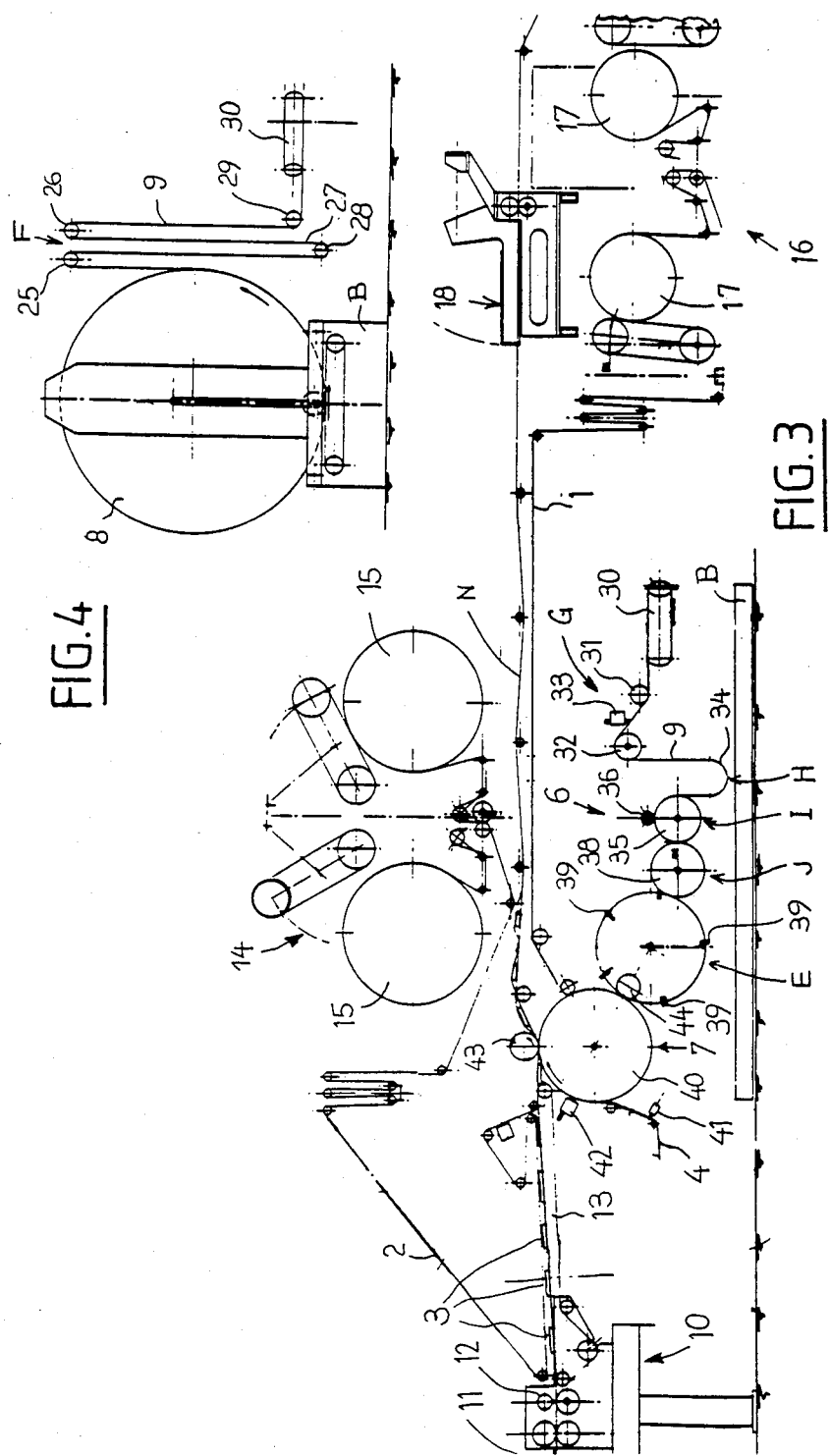

MACHINE FOR FASTENING STRETCHED PIECES OF ELASTIC BAND TRAVERSELY TO A CONTINUOUSLY MOVING SHEET

BACKGROUND OF THE INVENTION

1. Field of the Invention

The present invention relates to machines for fastening stretched pieces of elastic band to a sheet and to apparatuses for producing a composite sheet intended for providing diapers.

2. Description of the Prior Art

On an industrial scale, diapers are manufactured continuously by means of an apparatus in which a sheet of impermeable material, such as polyethylene, and a permeable sheet, such as of a non-woven material, are bonded to one another with uniformly spaced wads of absorbent material being interposed between these sheets.

The composite sheet formed in this way is subsequently cut transversely between the absorbent wads and each piece of the composite sheet, cut off in this way, is intended to form a diaper.

During this production, it is known to bond, between the two sheets, two elastic bands each of which extend longitudinally over the composite sheet at respective lateral ends of the latter. These elastic bands are bonded, when stretched between the sheet as flatly arranged, so that pleats or puckers are formed on the lateral edges of the diapers when slackened.

However, the bonding of stretched pieces of elastic band transversely between the two flatly arranged sheets, to product diapers provided with an elastic tape at each of their longitudinal ends, presents a problem in production.

In fact, the operation of bonding stretched pieces to a sheet at regular intervals so that these pieces of band extend in a transverse direction relative to the direction of movement of the sheet, is a difficult one inasmuch as the pieces of band have to be delivered regularly and stretched and laid on the sheet in such a manner that these pieces are bonded while extending and being stretched in a transverse direction relative to the direction of movement of the sheet.

SUMMARY OF THE INVENTION

The object of the invention is, therefore, to provide a machine for bonding stretched pieces of elastic band transversely to a sheet which operates reliably and efficiently, while at the same time allowing a high bonding rate of the pieces of band to be achieved.

Thus, the subject of the invention is a machine for fastening stretched pieces of elastic band to a sheet driven in a continuous movement, characterized in that it comprises, in a frame, means of supplying pieces of band which are intended for delivering pieces of band to means of stretching the latter and means for laying and fastening the stretched pieces of band on the sheet in the region of a bearing surface on which this sheet rests. The supply means is synchronized with the stretching means which are themselves synchronized with the drive means moving the sheet.

According to other characteristics:

The stretching means are mounted so as to be movable in terms of rotation about a first axis which is transverse relative to the direction of movement of the sheet.

The stretching means comprises respective means of retaining each lateral end of the pieces of band and means of shifting these respective retaining means relative to one another parallel to the first axis.

The shifting means is of the cam type.

The retaining means is of the gripper type associated with actuating means synchronized with the laying and fastening means and with the supply means.

Each of the respective means of retaining a lateral end of the pieces of band comprises at least one gripper device intended for retaining the lateral end of a piece of band, these devices being distributed circumferentially about the first axis and being arranged at one and the same radial distance from this axis. Each gripper device of each of the retaining means is located in one and the same angular position about the first axis as a corresponding associated gripper device of the opposite retaining means intended for retaining the opposite lateral end of the piece of band.

Each gripper device comprises a gripper which extends parallel to the first axis and the active end of which is oriented in the direction of the opposite associated gripper.

Each gripper is mounted pivotably on a respective support about an axis perpendicular to the first axis, between an active position, in which this gripper is capable of gripping the corresponding lateral end of a band between its active end and the corresponding support, and a released position, in which this active end of the gripper is away from the support. The actuating means comprises means of putting the gripper in the active position and means of releasing it.

The gripper supports are mounted slideably parallel to the first axis.

There are two flanges spaced axially on a shaft, on which they are wedged in terms of rotation. This shaft extends according to the first axis and the gripper supports of each of the retaining means are carried by respective flanges and are mounted slideably between these flanges.

Each gripper support is associated with a respective connecting rod, this connecting rod being articulated at each of its ends about axes parallel to one another on the corresponding support on the one hand and on the adjacent flange on the other hand.

The shifting means comprises two cams integral with the frame and spaced axially from one another between the two flanges. Each of these cams extends circumferentially around the first axis and the connecting rods carried by one and the same flange are each provided with a roller interacting with a corresponding cam to control the sliding of the respective gripper support.

The means of putting each gripper in the active position comprises a respective elastic member arranged between the gripper and the corresponding support to stress the active end of the gripper in the direction of the respective support.

Each gripper carries a roller and the releasing means comprises two pairs of cams integral with the frame, each associated with the grippers carried by one and the same flange. Each pair of cams comprises a first cam located in the vicinity of the laying and fastening means and a second cam located in the vicinity of the supply means.

The subject of the invention is also an apparatus for producing a composite sheet intended for providing diapers. This composite sheet comprises two sheets joined to one another between which pieces of elastic band are bonded transversely, being spaced from one another so as to be stretched on the composite sheet arranged flat and wads of absorbent material, each located between the sheet and two adjacent pieces of band. This apparatus comprises a machine for fastening the stretched pieces of elastic band transversely to the first sheet, means of arranging an absorbent wad between two adjacent pieces of band on the first sheet and means for fastening a second sheet to the first in such a way that the pieces of band and the wads extend between these two sheets. The apparatus is characterized in that the machine for fastening the stretched pieces of elastic band transversely to the first sheet is as defined above.

BRIEF DESCRIPTION OF THE DRAWINGS

The invention will be understood better from a reading of the following description of an embodiment given purely as an example and made with reference to the attached drawings in which:

FIG. 3 is a partial diagrammatic view of an apparatus according to the invention for the production of a composite sheet such as that shown in FIGS. 1 and 2, this apparatus including the machine according to the invention intended for bonding stretched pieces of elastic band to a continuously moving sheet;

FIG. 4 is a diagrammatic view of part of the means of supplying elastic band to the machine according to the invention which is included in the apparatus of FIG. 3;

DETAILED DESCRIPTION OF THE INVENTION

Description of the Composite Sheet

Figure 1:
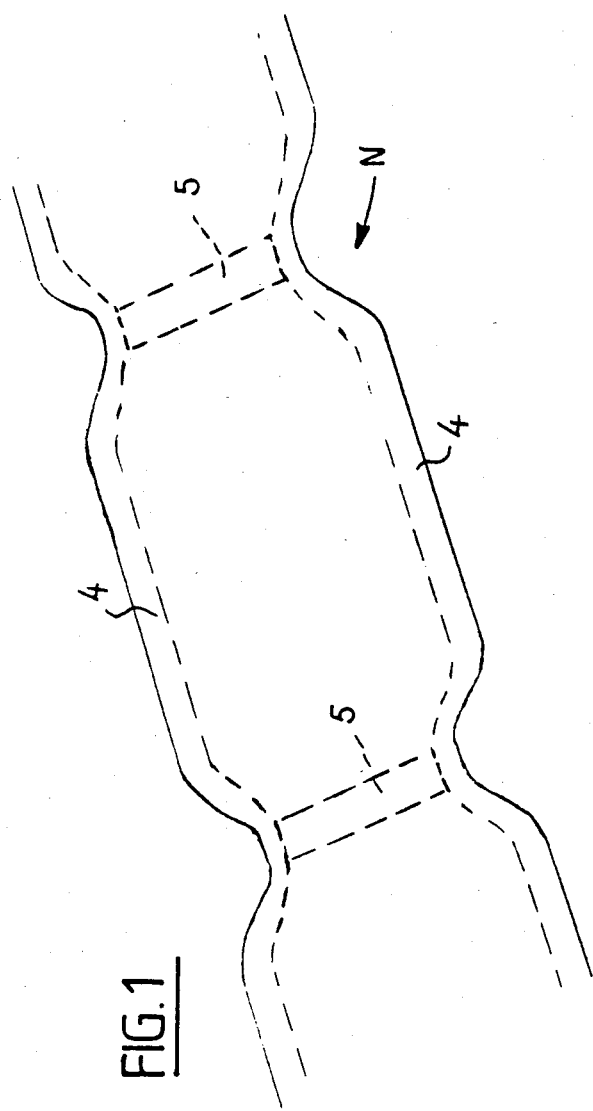
FIG. 1 is a diagrammatic plan view of a composite sheet which is intended for providing diapers and which can be produced by means of the apparatus according to the invention.
Figure 2:
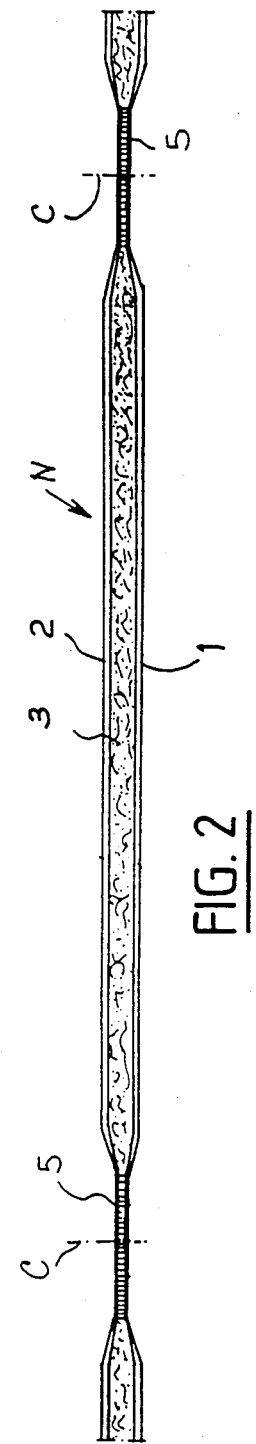
FIG. 2 is a view in longitudinal section of a composite sheet such as that shown in FIG. 1.

The composite sheet N illustrated in FIGS. 1 and 2 comprises a first sheet 1 made of a flexible and impermeable material, for example, polyethylene film, forming one face of the composite sheet, and a second sheet made of a flexible and permeable material, for example, a non-woven material, forming the other face of the composite sheet.

These two sheets 1 and 2 are joined to one another by bonding and wads 3 of absorbent material, elastic bands 4 and pieces of elastic band 5 are inserted between the two sheets 1 and 2 between which they are bonded.

Each elastic band 4 extends along a corresponding longitudinal edge of the composite sheet, being bonded in such a way that these elastic bands are stretched when the composite sheet is flat to form pleats or puckers extending longitudinally when this composite sheet is slackened. The pieces of elastic band 5 each extend transversely in the composite sheet between each longitudinal elastic band 4, being spaced from one another at regular intervals. These pieces of elastic band 5 are likewise bonded in such a way that they are stretched when the composite sheet is flat to form pleats or puckers extending transversely when this composite sheet is slackened.

The absorbent wads 4, for example, consisting of shredded wood pulp, each extend longitudinally between two adjacent pieces of elastic band and transversely between the two longitudinal elastic bands 4.

The elastic material used for the bands 4 and the pieces of band 5 can be any material currently used in this field cf the art but especially an elastic material consisting of open-cell foam, such as polyurethane foam.

This composite sheet, as described above, makes it possible to produce diapers if this composite sheet is cut along transverse lines C (FIG. 2), each located approximately in the middle of a piece of band so that a diaper is formed between two cutting lines C.

Description of the Apparatus

In diapers produced in this manner, the longitudinal elastic bands 4 are intended to extend around the user's thighs to ensure that the diaper is sealed in this region. The transversely bonded pieces 5 are intended to come around the user's waist, again, to ensure that the diaper is sealed.

The apparatus illustrated in FIGS. 3 and 4 intended for producing the composite sheet N includes a machine 6 intended for bonding the stretched pieces 5 of elastic band transversely to the first sheet 1 at an assembly station 7, the pieces 5 of elastic band being supplied from a roller 8 (FIG. 4) of elastic band 9, The apparatus also includes a station 10 for producing wads 3 from a sheet 11 of an absorbent material cut at regular intervals by known cutting means 12 of the rotary-knife type. The wads 3 are conveyed between the station 10 and the assembly station 7 by a conveyor 13 which deposits each wad 3 on the sheet 1 between two previously bonded pieces of band 5. The nonwoven sheet 2 is conveyed to the assembly station 7 from supply means 14 comprising two rollers 15 intended to be unreeled one after the other in succession.

The impermeable sheet 1 is likewise conveyed to the assembly station 7 from supply means 16 comprising two rollers 17 intended to be unreeled one after the other.

The assembled composite sheet N is conveyed from the assembly station 7 to a cutting station (not shown) to provide diapers passing beforehand through a device 18 for pressing this composite sheet N, this pressing device comprising two endless belts (not shown), between which the composite sheet is pressed.

Two bands 4 of elastic material are likewise conveyed to the assembly station 7, each to be bonded on either side along a corresponding longitudinal edge of the first sheet 1.

General Description of the Machine According to the Invention

The machine 6 comprises in an upstream direction, in a frame B which is partially shown, means D of supply pieces 5 of band 9 which are designed to deliver these pieces to a stretching station E adjacent to the assembly station 7 and intended for stretching the elastic pieces 5 before they are laid on the first sheet 1.

These supply means D comprise, again in the downstream direction, the roller 8 from which the band 9 is unreeled and a tensioning station F, where the band coming from the roller 8 is tensioned before penetrating into a glue-coating station G, at which the whole of one of the surfaces of this band is coated with glue, with the exception of two zones each located in the vicinity of a lateral end of the band.

The glue-coating station G is followed by a relaxing station, where the band 9 is slackened before being fed to a cutting station I, where the band is cut transversely at regular intervals over its length into pieces 5 which are distributed to a transfer station J designed to transfer the pieces 5 from the cutting station I to the stretching station E in order to supply the latter.

The roller 8 is mounted rotatably about a horizontal axis and the strand of band 9 coming from this roller rises to pass over a first guide roller 25 descends again and rises again to pass over a second guide roller 26 forming a loop 27 between these two guide rollers 25 and 26. A tensioning roller 28 is arranged at the bottom of this loop 27 to ensure the tensioning of the band 9. This tensioning roller 28 can act solely by means of its own weight or can be associated with a tension spring (not shown).

After passing over the second guide roller 26, the band 9 passes over a first deflecting roller 29 (FIG. 4) which preserves the direction of movement of the band and over a second deflecting roller 30, by means of which the direction of movement of the band is deflected at right angles. This arrangement, which makes use of the second deflecting roller 30, advantageously makes it possible to limit the space taken up by the length of the machine by arranging the roller 8 on one side of the latter.

The band, tensioned in this way by the roller 28 is oriented by the second deflecting roller 30, passes under a third guide roller 31 and rises again in an inclined direction to pass over a fourth guide roller 32, and between these third and fourth guide rollers 31 and 32 respectively a nozzle 33 applies glue to the upper surface of the band 9.

When it leaves the fourth guide roller 32, the glue-coated band 9 descends again and immediately rises again up to the cutting station 1. Thus, the bandrelaxing station H is provided between the cutting station and the fourth guide roller 32 by a loop 34, the presence of which ensures that the band 9 is slackened in this region.

The cutting station I comprises a device forming an anvil 35 and a cutting device 36 which are mounted rotatably about axes parallel to one another. The band 9 passes between the cutting device 36 and the device forming an anvil 35 to be cut transversely into pieces 5 of band.

The pieces 5 of band 9 are subsequently transferred to the stretching station E by means of fingers 37 (FIGS. 5 and 10) which are carried by a drum 38 mounted rotatably about an axis parallel to the axis of rotation of the device forming an anvil 35. These fingers 37 interact with the glue-coated surface of the pieces 5 of band and, as a result of the rotation of the drum 38, these pieces 5 of band are transferred to the stretching station E where they are each grasped at their lateral ends by a pair of grippers 39. These grippers 39 are mounted rotatably about an axis parallel to the axis of rotation of the drum 38 of the transfer station J and the pieces 5 of band will be stretched parallel to this axis in order to be laid on and bonded to the first sheet 1 at the assembly station 7.

This assembly station 7 comprises a drum 40 adjacent to the stretching station E and mounted movably in terms of rotation about an axis parallel to that about which the grippers 39 are mounted rotatably.

If the direction of rotation of the drum 40 is considered, the composite sheet N is assembled on the periphery of this drum 40 in the following sequence:

First, the first sheet 1 is laid on the cylindrical surface of the drum 40 with which it moves, the pieces 5 of band are bonded to the first sheet extending transversely relative to its direction of movement and being spaced uniformly from one another, the longitudinal elastic bands 4, previously coated with glue by means of a nozzle 41, are applied to each of the lateral ends of the first sheet 1, a series of nozzles 42 deposits strands of glue on the pieces 5, the elastic band 4 and the first sheet 1 itself, the conveyor 13 deposits the absorbent wads 3 between the pieces 5 of band in the region of the upper part of the drum 40, the wads 3 are subsequently covered by the second non-woven sheet 2, and the assembly as a whole is bonded to form the composite sheet N when it passes between the drum 40 and a pinching roller 43.

The stretched pieces 5 are laid on and fastened to the first sheet 1 by being pinched between this first sheet, supported by the drum 40, and two laying and fastening rollers 44 (FIGS. 3, 7, 8, 9 and 10) which extend between the grippers 39 of the stretching station E. The part of the cylindrical surface of the drum 40 where the rollers 44 for laying on the pieces 5 are applied to the sheet, thus forms a bearing surface during the bonding of the pieces 5 ot the first sheet 1.

Of course, the means of supplying absorbent wads 3, the means of supplying the second non-woven sheet 2, the means of supplying the first sheet 1 of impermeable film, the means E of stretching the pieces 5 and the means of laying on and fastening the latter are synchronized with the operating speed of the assembly station 7, that is to say, the rotational speed of the drum 40 which drives the sheet 1 in its advancing movement.

Description of the Synchronizing Means

Figure 5:
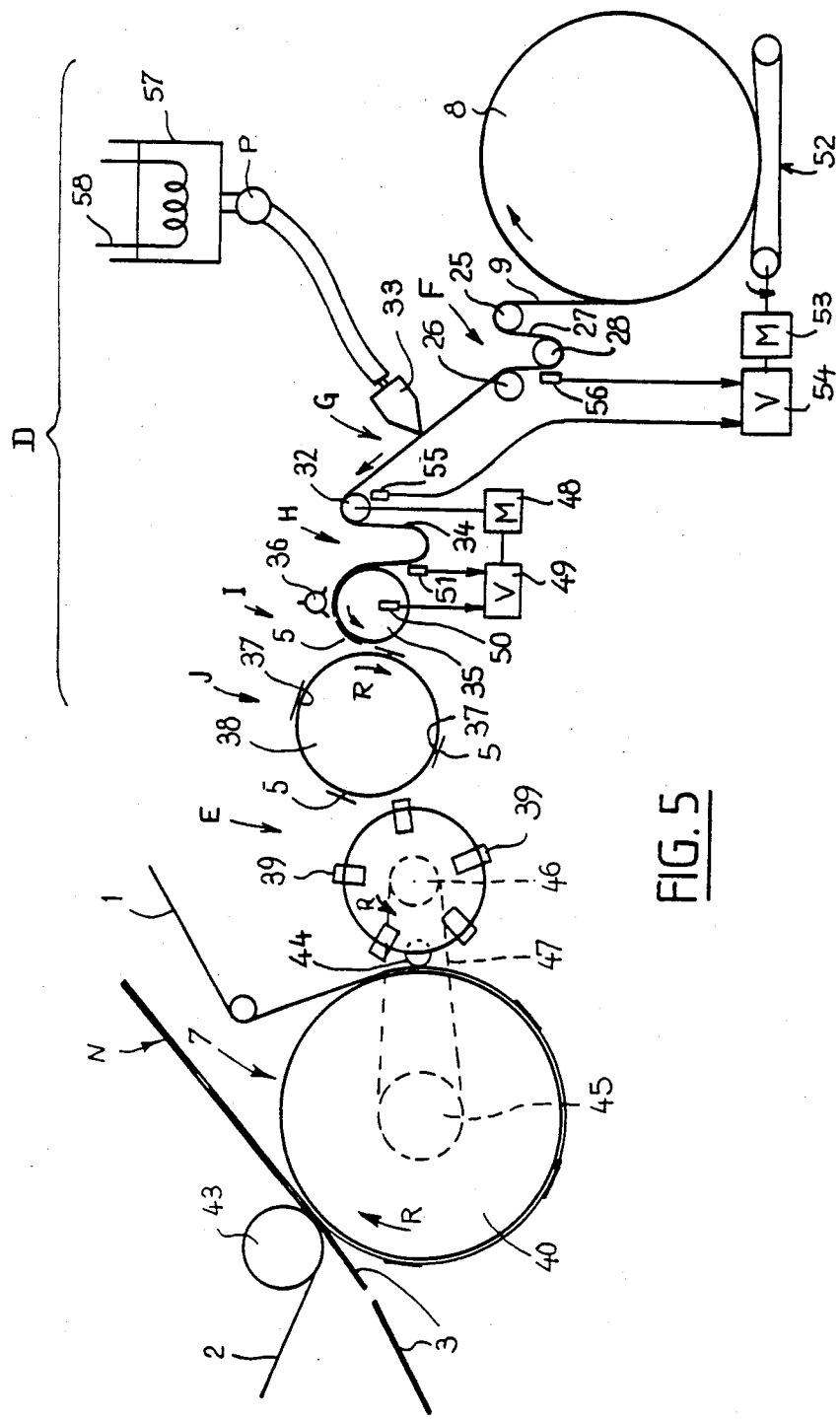
FIG. 5 is a simplified basic diagram, on a larger scale, of the mahcine according to the invention included in the apparatus of FIGS. 3 and 4.

The drum 40 driven in rotation by a device (not shown) itself drives in rotation the grippers 39 of the stretching station E by means of a variable mechanical transmission device without slip of the conventional type, which comprises two pulleys each having an axially movable flange and connected to one another by a chain (FIG. 5). A first pully 45 is integral with the drum 40 in terms of rotation and the axial position of the movable flange of this pulley in relation to the associated fixed flange is adjusted by means of a jack or a conventional mechanical actuation device. A second pulley 46 is integral with the grippers 39 in terms of rotation, the movable flange of this pulley 46 being stressed towards the adjacent fixed flange by means of an elastic member.

The inner faces of the flanges of these pulleys are each provided with radial ribs which interact with lateral fingers projecting from the chain 47 connecting the pulleys 45 and 46. By means of this arrangement, the stretching station E for the pieces 5 of band is synchronized variably with the assembly station 7 inasmuch as the winding radius of the chain 47 on each of the pulleys 45 and 46 is variable. The variability of the ratio of the operating speeds of these two stations thus makes it possible to adjsut the spacing between the pieces 5 of band bonded to the first sheet 1 so that diapers of different lengths can be produced.

The fourth guide roller 32 is driven in rotation by means of a motor 48 controlled by a speed variator 49. This variator 49 regulates the speed of the fourth guide roller 32 on the one hand as a function of the rotational speed of the device forming an anvil 35 of the cutting station I by means of a speed sensor 50, for example, of the mechanical or electronic type, connected to the variator 49 and on the other hand as a function of the position of the bottom of the loop 34 of the station H relaxing the elastic band 9 by means of a position sensor 51, for example, of the mechanical or electronic type, likewise connected to this variator 49 (FIG. 5).

This arrangement makes it possible to synchronize the fourth guide roller 32 with the cutting station I, while ensuring the constant presence of the loop 34 in the relaxing station H.

The roller 8 of elastic band 9 is unreeled by means of an endless belt 52 driven by a motor 53 controlled by a speed variator 54. This variator 54 regulates the speed of the motor 53 on the one hand as a function of the rotational speed of the fourth guide roller 32 by means of a speed sensor 55, for example, of the mechanical or electronic type, connected to the variator 54 and on the other hand as a function of the position of the bottom of the tensioning loop 27 of the band 9 by means of a position sensor 56, for example, of the mechanical or electronic type, connected to the variator 54.

This arrangement makes it possible to synchronize the unreeling speed of the roller 8 with the drive speed of the fourth guide roller 32, while ensuring that the band 9 is correctly tensioned upstream of this guide roller by controlling the position of the bottom of the loop 27.

At the glue-coating station 23, the nozzle 33 is connected, by means of a pump P (FIG. 5), to a tank 57 containing hot glue kept in the molten state by means of an electrical resistor 58. The flow of glue delivered by the pump P is adjusted on the one hand as a function of the required thickness of glue on the band 9 and on the other hand as a function of the speed of movement of the latter.

Figure 6:
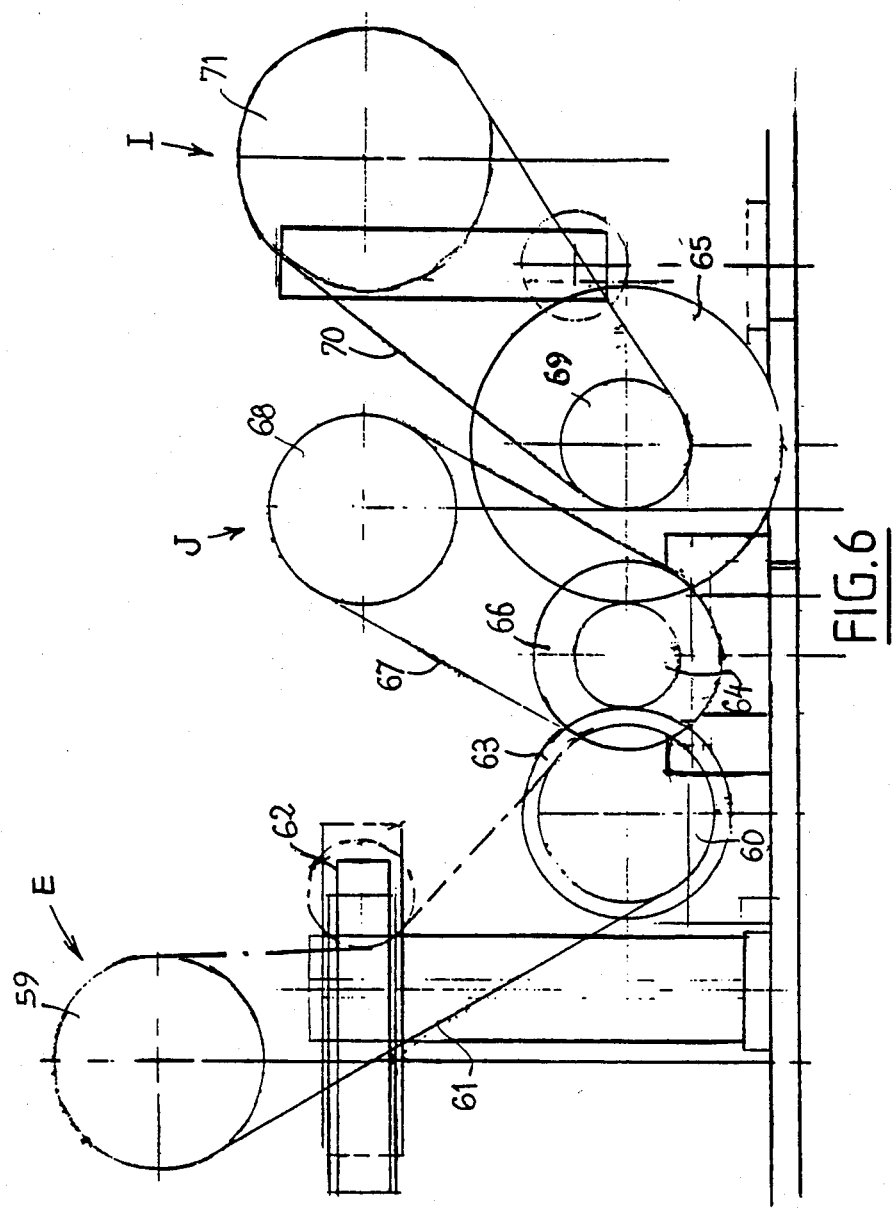
FIG. 6 is a diagrammatic view of the means of driving and synchronizing the transfer stations and of cutting the pieces of band of the machine according to the invention.

The grippers 39 of the stretching station E are integral in terms of rotation with a gear wheel 59 (FIG. 6). This gear wheel 59 is connected to a second gear wheel 60 by means of a chain 61, one strand of which is tensioned by means of a tensioning pinion 62. The gear wheel 60 is integral with a pinion 63 meshing with a second pinion 64 which itself meshes with a third pinion 65.

The second pinion 64 is integral in terms of rotation with a third gear wheel 66 connected by means of a chain 67 to a fourth gear wheel 68 integral in terms of rotation with the drum 38 supporting the fingers 37 of the transfer station J.

The third pinion 65 is integral in terms of rotation with a fifth gear wheel 69 connected, by means of a chain 70, to a sixth gear wheel 71 integral in terms of rotation with the device forming an anvil 35 of the cuttong station I.

The rotational speed of the device forming an anvil 35 of the cutting station I is thus synchronized with that of the drum 38 of the transfer station J, the rotational speed of this drum 38 itself being synchronized with that of the grippers 39 of the stretching station E.

It is appropriate to note that the direction of rotation of the drum 40 of the assembly station 7 and that of the drum 38 of the transfer station J are identical. Likewise, the direction of rotation of the grippers 39 of the stretching station E and that of the device forming an anvil 35 of the station I are identical and opposite to that of the drum 40 of the assembly station 7 (see the arrows R in FIG. 5).

Figure 7:
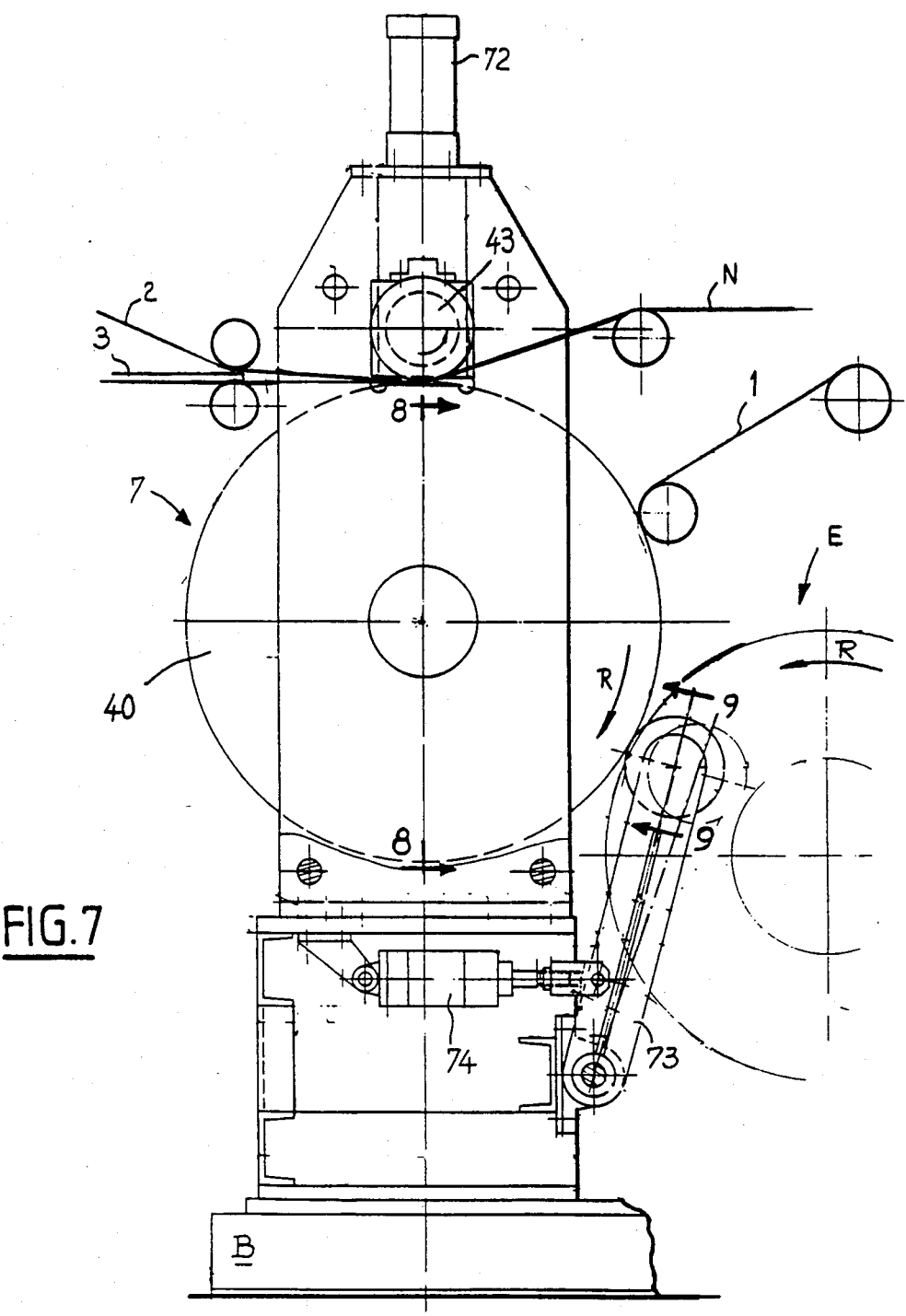
FIG. 7 is a diagrammatic side elevational view, on a larger scale, of the composite sheet assembly station of the apparatus illustrated in FIG. 3.

Detailed Description of the Machine According to the Invention, the Assembly Station and the Laying and Fastening Means The drum 40 of the assembly station 7, as illustrated in FIG. 7, is horizontally mounted rotatably between two pillars of the frame B. The pinching roller 43 is likewise mounted rotatably between these two pillars of the frame B about an axis parallel to that of the drum 40 in such a way that its cylindrical surface is approximately tangent to that of the drum 40 so that the elements of the composite sheet N are pinched between this roller 43 and the drum 40 so as to be assembled together by bonding.

Figure 8:
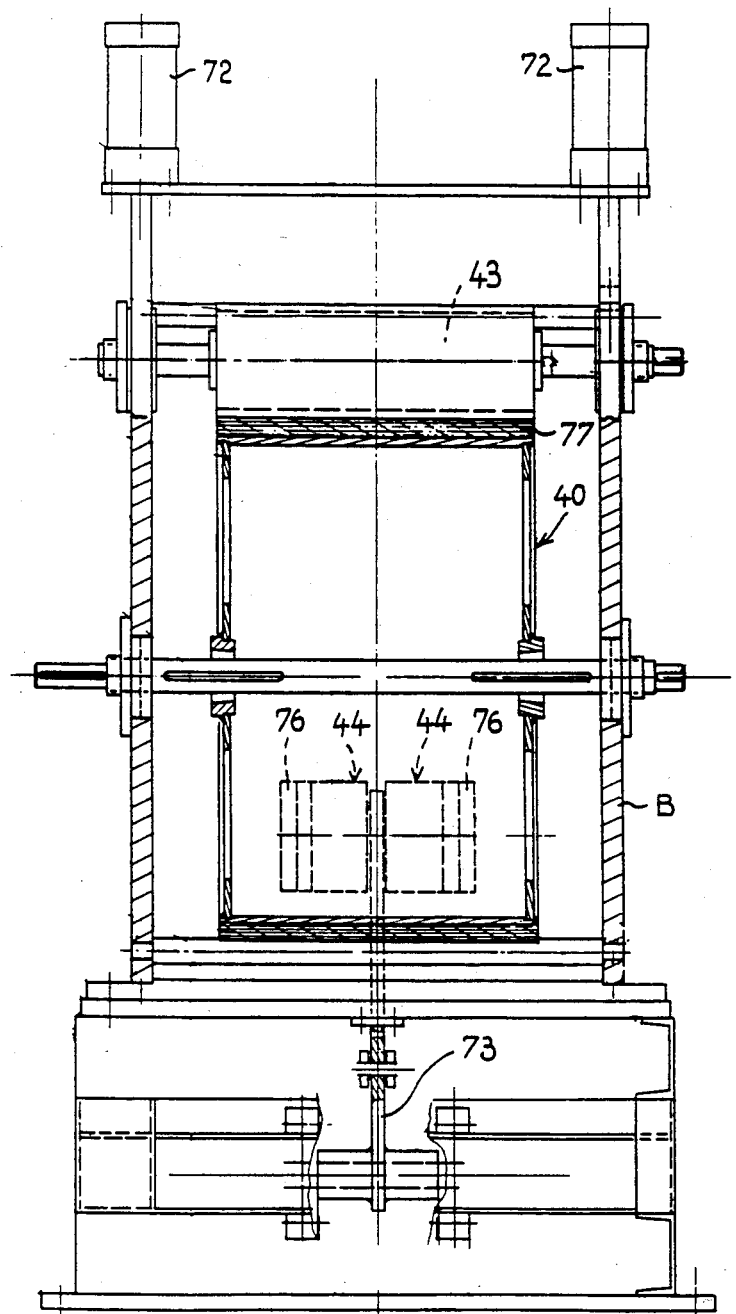
FIG. 8 is a view in a partial section along the line 8—8 of FIG. 7 partially cut away.

The force with which the pinching roller 43 is applied against the drum 40 can be adjusted by means of two jacks 72 (FIGS. 7 and 8).

The rollers 44 laying the stretched pieces 5 of elastic band 9 on the first sheet 1 supported by the drum 40 are each mounted rotatably about one and the same axis parallel to the axis of rotation of the drum 40. The rollers 44 are carried in the vicinity of one end of an arm 73, being arranged on either side of this arm. The arm 73 extends perpendicularly relative to the rollers 44 towards the lower part of the frame on which it is articulated, at its end opposite the rollers 44 about an axis parallel to the axis of rotation of the latter.

These rollers 44 are pressed against the first sheet 1, bearing on the drum 40 by means of a jack 74 articulated at one of its ends on the arm 73 and, at its opposite end, on the frame B. The jack 74 thus makes it possible to adjust the force with which the stretched pieces 5 of elastic band will be pinched between the first sheet and these laying rollers 44 so as to be bonded to this sheet.

Figure 9:
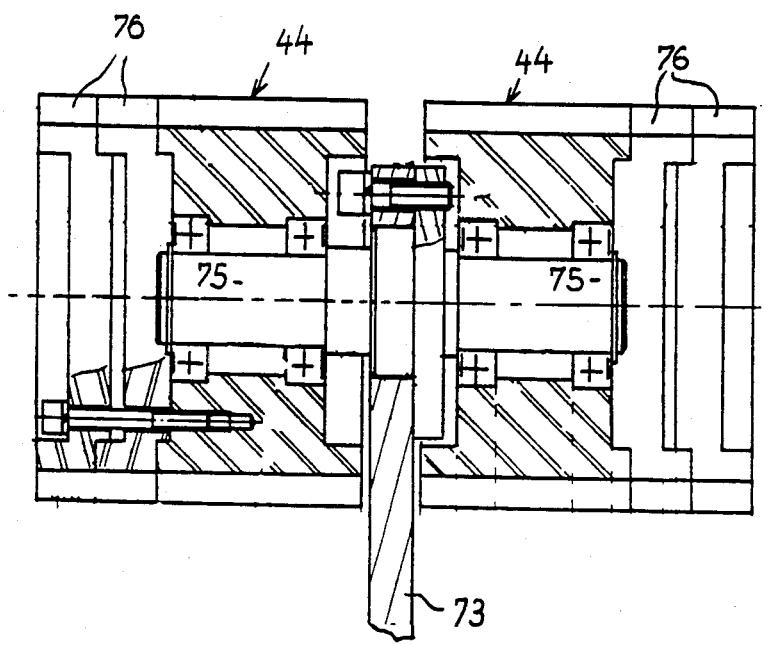
FIG. 9 is a view, on a larger scale, in a partial section along the line 9—9 of FIG. 7.

As shown in more detail in FIG. 9, the corresponding end of the shaft 73 carries two tail shafts 75 which each extend according to one and the same axis in opposite directions to one another. Each of the rollers 44 is mounted rotatably on one of these tail shafts 75 and is capable of receiving at its axial end opposite the arm 73 at least one annular member 76 designed to increase the axial length of the corresponding roller 44 as a function of the length of the stretched pieces 5 or, in other words, as a funxtion of the width of the elastic band 9, from which the pieces 5 are produced.

Referring again to FIG. 8, it will be noted that the cylindrical surface of the drum 40 has a covering 77 consisting of a material with a high coefficient of friction and a low coefficient of adhesion, for example, silicone rubber, so that the first sheet 1 remains stretched on the periphery of the drum 40 between the laying rollers 44 and the gripping roller 43 counter to the elastic force exerted by the bonded pieces 5 which are stretched over this first sheet and which tend to retract it laterally. The first sheet 1 is thus held laterally on the covering 77 of the drum 40 by means of friction so that it is completely flat when it receives the longitudinal elastic bands 4 and penetrates under the gripping roller 43.

Stretching Station

The stretching station E has a shart 78 mounted rotatably about an axis parallel to the axes of rotation of the drum 38 of the transfer station J and of the drum 40 of the assembly station 7, this shaft 78 carrying, wedged in terms of rotation, two flanges 79 spaced axially and extending in a plan perpendicular relative to their axis of rotation.

In this embodiment, each flange 79 carries five grippers 39 each extending parallel to the shaft 78 in the direction of the opposite flange, that is, the active end of the grippers carried by one flange oriented in the direction of the opposite flange. Each of the grippers carried by a flange 79 is located in one and the same angular position relative to the shaft 78 as a corresponding gripper 39, which is carried by the opposite flange 79 and with which it forms a pair. Stretching station E thus comprises five pairs of grippers spaced at equal angular intervals around the shaft 78, each of the grippers of one and the same pair of grippers being intended to retain a corresponding lateral end of the pieces 5 of elastic band.

Each gripper is articulated on a support 80 about an axis perpendicular to the axis of rotation of the shaft 78.

These supports 80, spaced at equal angular intervals around the shaft 78, are each mounted slideably between the two flanges 79 by means of two guide rods 81 which pass through the corresponding flange 79 and which slide in respective blocks 82 fastened to the outer face of this flange 79.

Each gripper 39 has a width near that of the pieces 5 of band and is articulated on a corresponding support 80, being received in a fork provided in this support, the grippers 39 being arranged radially on the outside of the flanges 79.

A helical spring 83 is fastened at one of its ends to the bottom of the fork provided in each support 80 and, at its opposite end, to the corresponding gripper 39 between the axis of articulation of the latter on the support and its active end. Each spring 83 operates by extension so as to return the respective gripper 39 towards its active position, that is, the position in which the active end of this gripper is up against the corresponding support, in order to grip a lateral end of a piece 5 of elastic band between the latter support and this active end.

Figure 12:
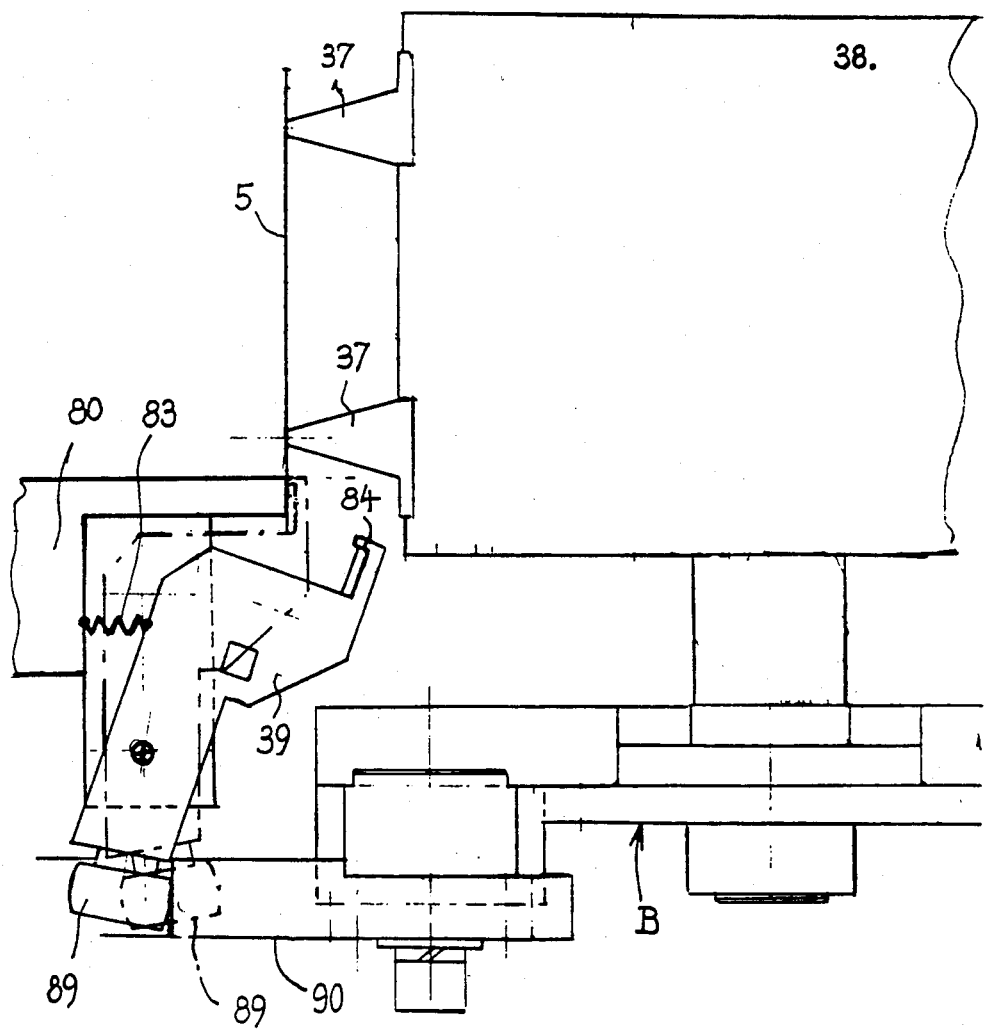
FIG. 12 is a detail view of part of FIG. 10 on a larger scale illustrating the passage of the pieces of band from the trnasfer station to the stretching station.

Referring to FIG. 12, it will be seen that the active end of the grippers 39 has a rib 84 extending along the width of the gripper to form a type of nose by means of which these grippers grip the lateral ends of the pieces 5 of band against the supports 80.

To control the sliding of the supports 80 parallel to the axis of the shaft 78, each of the supports is associated with a connecting rod 85 which is articulated at each of its ends about axes parallel to one another, on the one hand on the corresponding support 80 and on the other hand on the flange 79 carrying this support. Each connecting rod 85 carries a roller 86 mounted movably in terms of rotation about a radial axis parallel to the axes of articulation of the ends of the respective connecting rod 85.

The rollers 86 associated with the connecting rods 85 carried by one and the same flange 79 each interact with a cam 87 taking the form of a circumferential groove made in the outer periphery of a corresponding end of a sleeve 88 through which the shaft 78 passes and which is wedged on the frame 8.

The sleeve 88 thus forms at each of its ends a cam 87 which approximately delimits a sinusoidal period on the circumference of the sleeve. These cams 87 are symmetrical relative to a plan perpendicular to the axis of rotation of the shaft 78.

The cams 87 have such a profile that, as a result of the sliding of the supports 80, the grippers of each pair of grippers 39 arranged in the same angular position relative to the shaft 78 are brought closer to one another when they are in the vicinity of the transfer station J forming between them a space of a length slightly less than that of the pieces 5 of band so that each gripper of this pair of grippers can grip against the corresponding support 80 a respective lateral end of a piece 5 of band presented by the transfer station J.

Moreover, the profile of these cams 87 is such that they move the two grippers 39 of one and the same pair of grippers axially away from one another during the rotation of this pair of grippers in the angular gap located between the transfer station J and the assembly station 7, thereby stretching the piece 5 of elastic band grasped by each of its lateral ends at the transfer station J. When a pair of grippers is in the vicinity of the assembly station 7 opposite the first sheet 1 bearing on the drum 40, the grippers of this pair of grippers are as far away from one another as possible so that the laying rollers 44 extend between these and the support 80.

Furthermore, the cylindrical shell delimited by the supports 80 around the shaft 78 is approximately tangent to the cylindrical shell delimited by the fingers 37 around the axis of rotation of the drum 38 of the transfer station so that the lateral ends of the pieces 5 of band transferred by the fingers 37 come approximately in contact with the supports 80 on which they are to be gripped by the corresponding grippers 39. Likewise, the cylindrical shell delimited around the shaft 78 by the grippers in the active position is approximately tangent to the cylindrical shell delimited by the drum 40 so that the stretched pieces 5 of elastic band can be gripped between the laying rollers 44 and the first sheet 1 during the rotation of these grippers 39 together with the shaft 78.

The actuation of the grippers between their active position and their tight position, that is, respectively the position in which their active end is up against the corresponding support 80 counter to the force exerted by the respective spring 83 and the position in which the springs 83 move their active end away from the corresponding support, is carried out in synchronism with their axial displacement by means of a cam device.

Each gripper 39 thus has, at its end opposite the corresponding active end, a roller 89 mounted rotatably about an axis perpendicular to the axis of articulation of the corresponding gripper on the respective support 80.

Figure 10:
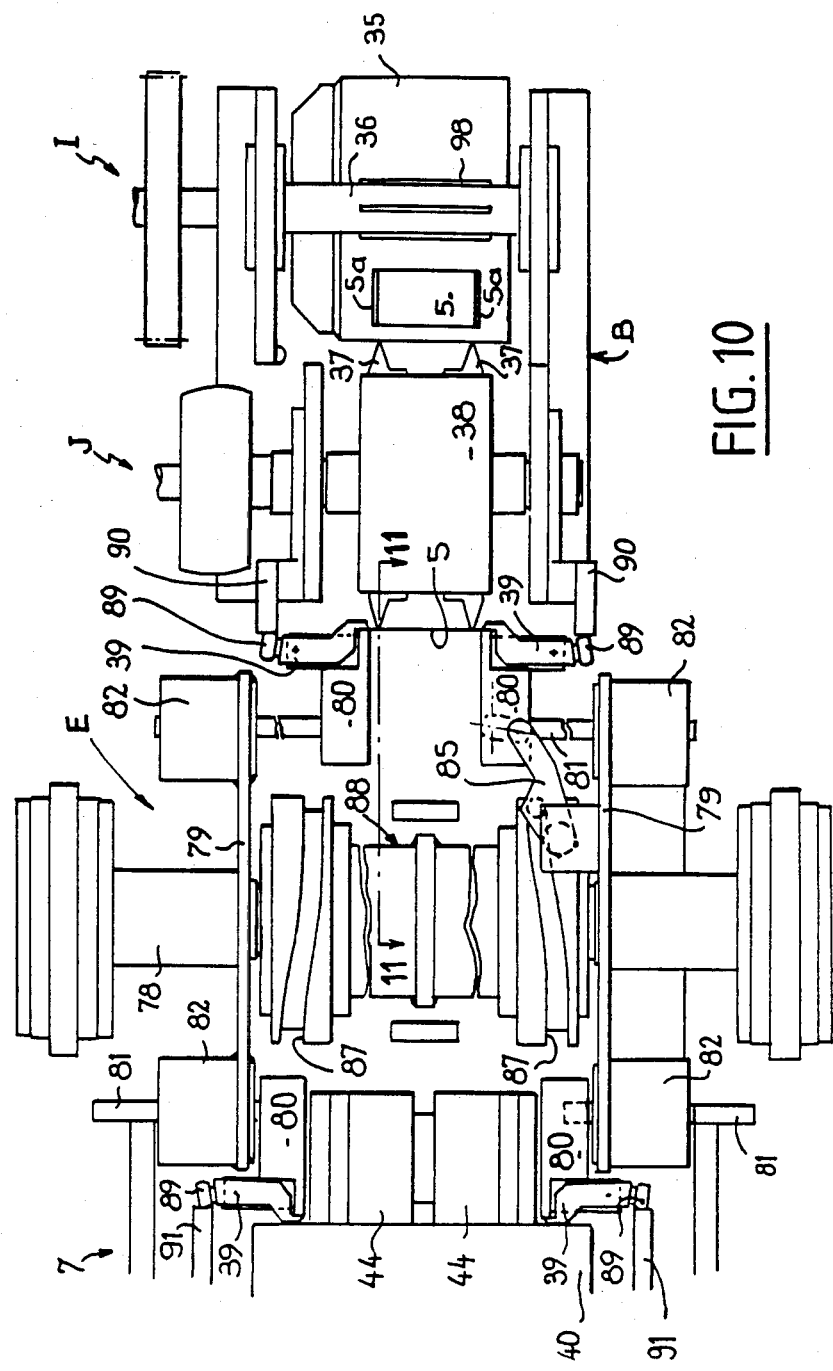
FIG. 10 is a plan view from above the machine according to the invention, partially illustrating the assembly, laying, stretching, transfer and cutting stations of this machine.
Figure 11:
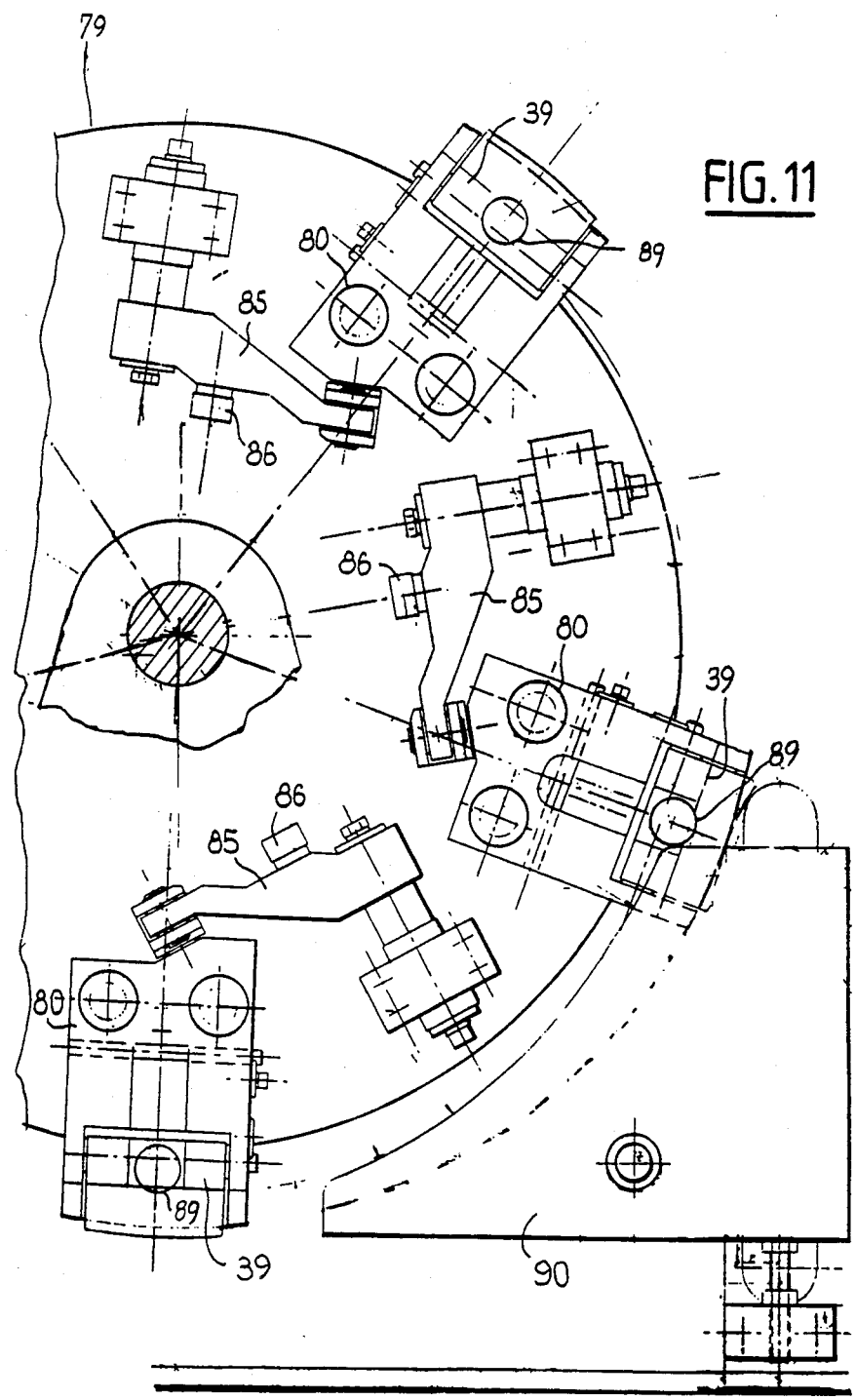
FIG. 11 is a diagrammatic view, on a larger scale, in a section along the line 11—11 of FIG. 10.

The rollers 89 carried by the grippers 39 associated with one and the same flange 79 are each designed to interact with two corresponding cams integral with the frame B (FIGS. 10, 11 and 12).

Thus, two first cams 90 are each provided on a corresponding side of the frame in the vicinity of the transfer station J and two second cams 91 are, likewise, each provided on a corresponding side of the frame in the vicinity of the assembly station 7.

These first and second cams 90 and 91 each have a curved profile and are intended to bring the grippers 39 into the released position when the rollers 89 come up against these cams 90 or 91.

The angular position of the cams 90 around the shaft 78 and the angular interval at which they extend around this shaft are such that the grippers of each pair of grippers are in the released position when they are opposite the transfer station J to grasp a piece 5 of band there, while being in the active position before arriving opposite this transfer station and when moving away from it. This characteristic is illustrated in FIG. 12 where the roller 89 of the gripper 39, shown in the released position by an unbroken line, interacts with the cam 90. This same gripper is represented by a dot-and-dash line in its active position in which the roller 89 no longer interacts with the cam 90 and in which a corresponding lateral end of a piece 5 of band is gripped against the corresponding support 80 by the active end of this gripper.

The angular position around the shaft 78 and the angular interval at which the second cams 91 extend around this shaft are such that the grippers 39 are brought into the released position when the stretched pieces 5 of elastic band, which they retain at their lateral ends, are gripped between the laying rollers 44 and the first sheet 1 supported by the drum 40, the grippers 39 being in the active position before the pieces 5 of band are laid on the sheet, and returning into this active position after these pieces 5 of band have been laid on this sheet.

Transfer Station

The drum 38 of the transfer station J has several pairs of radial fingers 37 delimiting a cylindrical shell around the axis of rotation of this drum 38 which is approximately tangent to the device 35 forming an anvil of the cutting station 1.

The fingers 37 of one and the same pair of fingers are spaced axially from one another on the drum 38 and each of these fingers is in such an axial position relative to the stretching station E and relative to the device forming an anvil 35 of the cutting station I so that the fingers 37 of a pair of fingers come up against the glue-coated surface of the pieces 5 of band between the two lateral glue-free parts 5a (FIG. 10) of these pieces 5, this pair of fingers presenting a piece 5 of band to a pair of grippers 39 of the stretching station E, in such a way that each of the grippers 39 of this pair of grippers grips against its respective support 80 a corresponding glue-free lateral end 5A of the pieces 5 of band (FIG. 10).

In other words, the axial distance between two fingers 37 of one and the same pair of fingers is less than that between two grippers 39 of one and the same pair of grippers when these grippers are in the position close to one another opposite the transfer station J.

Cutting Station

Figure 13:
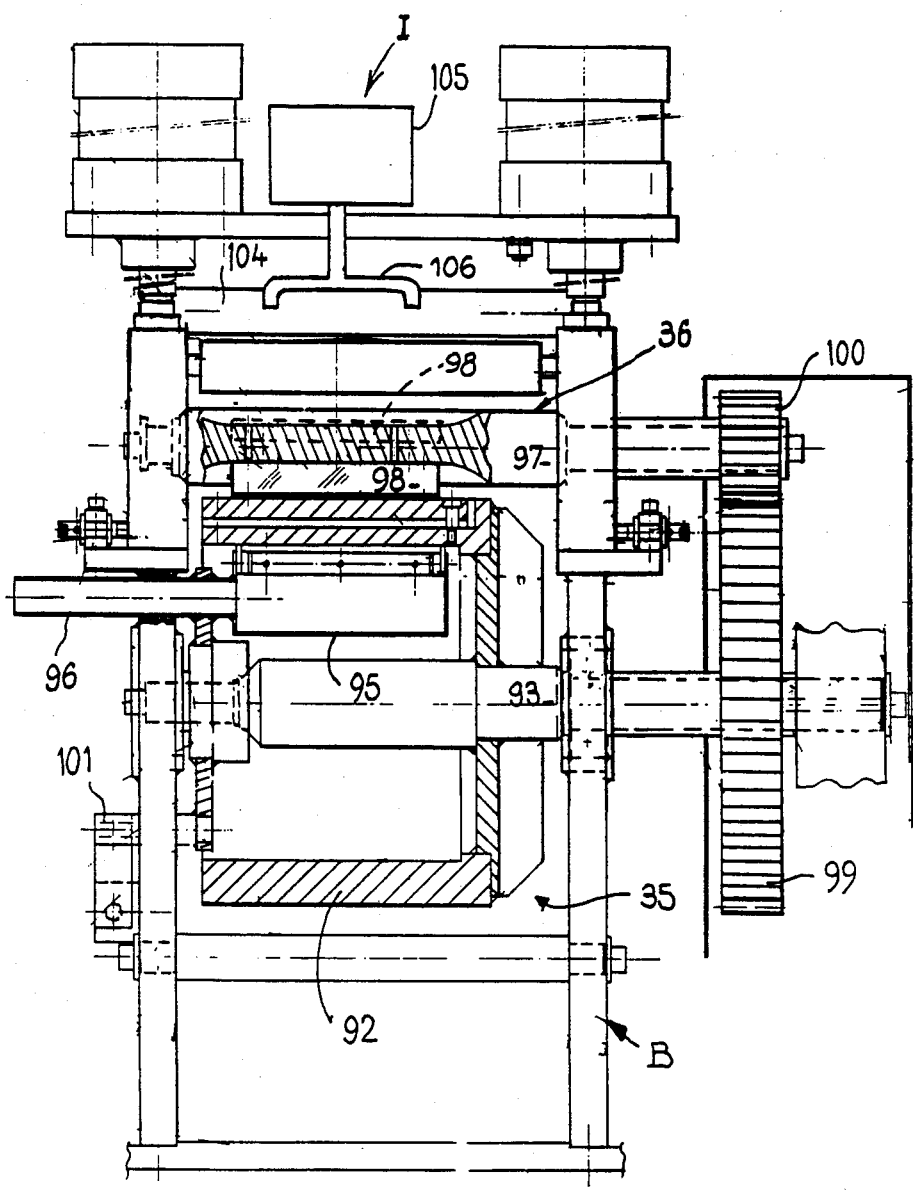
FIG. 13 is a view in a partial section along the line 13—13- of FIG. 14.
Figure 14:
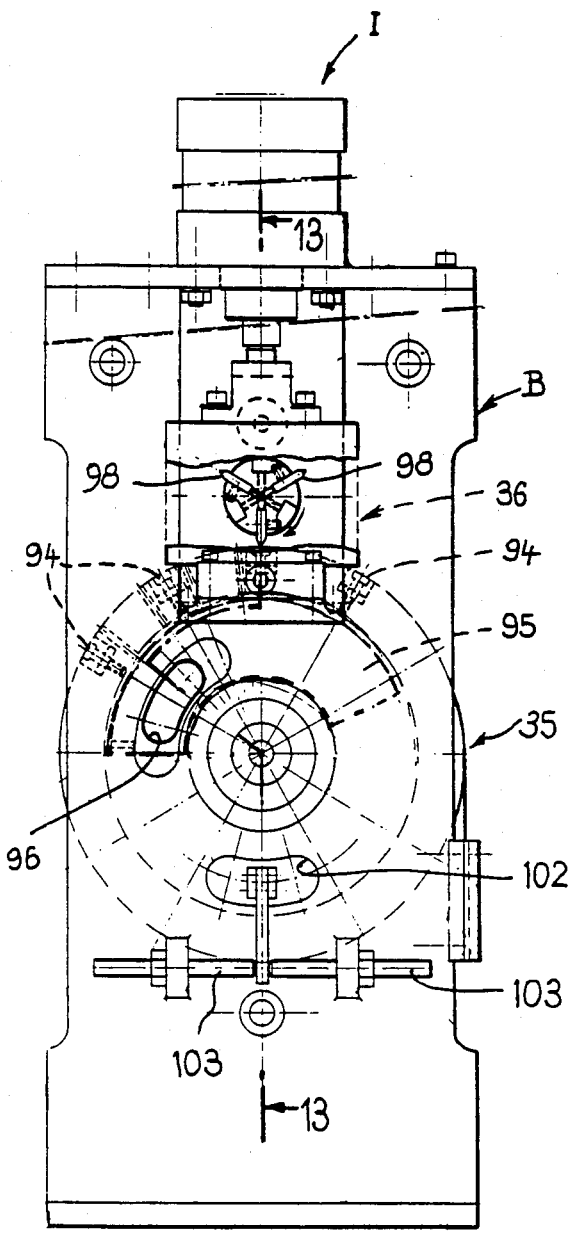
FIG. 14 is a diagrammatic side elevation view on a larger scale of the cutting station of the machine illustrated in FIG. 3; and, FIG. 15 is a diagrammatic perspective view illustrating al alternative embodiment of the stretching means.

The cutting station I illustrated in FIGS. 13 and 14 comprises between two pillars of the frame B, the device forming an anvil 35 arranged underneath the cutting device 36.

The device forming an anvil 35 comprises a bell 92 integral in terms of rotation with a shaft 93 swivelling in the frame B. This bell 92 is equipped, on its outer cylindrical surface, with anvil elements 94 (FIG. 14) in the form of processed-steel bars built into the bell 92 extending axially and spaced from one another circumferentially at equal angular intervals in such a way that the outer surface of these anvil elements 94 ensures the continuity of the outer cylindrical surface of the bell 92.

The cylindrical wall of this bell 92 is also provided with perforations (not shown) distributed over this entire wall between the anvil elements 94 and a suction nozzle 95 connected to an aspirator (not shown) by means of a pipe 96 and arranged inside the bell 92, the pipe 96 passing through the open face of this bell.

The suction nozzle 95 extends axially in the bell near the cylindrical inner surface of the latter and has the form of an angular sector so as to extend circumferentially in the vicinity of part of the cylindrical wall of the bell 92, being oriented approximately in the direction of the cutting device 36, that is, upwards in FIGS. 13 and 14, in order to retain on the outer cylindrical surface of the bell 92 by means of suction, the elastic band 9 and the pieces 5 produced as a result of the transverse cutting of the latter elastic band.

The cutting device 36 has a shaft 97 mounted rotatably in the frame B parallel to the shaft 93 of the device forming an anvil 35, being contained in one and the same vertical plane as this shaft 93.

The shaft 97 carries, radially, three knives 98 spaced circumferentially at equal angular intervals, the cutting edge of these knives extending axially. The cylindrical shell delimited by the knives 98 around the shaft 97 is approximately tangent to the outer cylindrical surface of the bell 92 so that, as a result of the rotation of the shafts 93 and 97 in opposite directions to one another, the band 9, retained by means of suction on the outer cylindrical surface of the bell 92, is progressively cut into pieces 5 by the knives 98 in the region of the anvil elements 94, these pieces 5 of band themselves being retained by means of suction on the outer cylindrical surface of the bell 92 until they are grasped by the fingers 37 of the transfer station J.

The shaft 93 is integral with a pinion 99 (FIG. 13) meshing with a pinion 100 integral in terms of rotation with the shaft 97 of the cutting device so that the latter is driven in rotation in the opposite direction to the shaft 93, while at the same time being synchronized with the latter.

A lever 101 articulated on the shaft 93 carries the nozzle 95 at one of its ends inside the bell 92 and at its opposite end extends outside the frame B through a slot 102 to be wedged between two adjusting nuts 103 which make it possible, by changing the angular position of the lever 101 around the shaft 93, to change that of the nozzle 95 in relation to the drum 38 of the transfer station J.

Since the surface of the band 9 oriented towards the knives 98 is that which has previously been coated with glue, these knives 98 are, therefore, liable to be soiled by the glue during the cutting of the band 9. For this purpose, a cylindrical brush 104 is arranged above the shaft 97 and is contained in one and the same vertical plane as this shaft so that, during their rotation, the knives 98 are cleared of glue by rubbing against this brush 104.

To maintain the efficiency of the brush 104 during operation, a tank 105 of suitable cleaning fluid, for example, paraffin, is arranged on the frame above the brush 104, the bottom of this tank being connected to a sprinkler rack 106 located above the brush 104, to spread the cleaning fluid contained in the tank 105 onto it drop by drop.

Operation

During operation, the band 9 unreeled from the roller 8 is tensioned longitudinally by the tensioning roller 28 and is then coated with glue on its upper surface at the glue-coating station G, while two lateral parts 5a are left free of glue.

After passing over the guide roller 32, the band 9 is slackened in the region of the loop 34 and is then retained by means of suction on the outer cylindrical surface of the bell 92 where it is progressively cut transversely by the knives 98 into pieces 5 retained on this bell 92 by means of suction.

Each piece 5 is subsequently grasped by a pair of fingers 37 of the transfer station J at the moment when this piece leaves the suction zone of the nozzle 95.

Arriving opposite the stretching station E, each piece 5 of band carried by a pair of fingers 37 meets tangentially a pair of grippers 39, of which the grippers are brought into the released position by the cams 90 and then immediately returned to the active position, moving away from these cams, in order to grasp the glue-free lateral ends of the piece 5 of band.

During the rotation of the shaft 78, the pieces 5 previously grasped by the grippers 39 at the transfer station J are progressively stretched because the grippers of each pair of grippers move axially away from one another, the latter being as far apart as possible when the pieces 5 of band are engaged between the laying rollers 44 and the first sheet 1 driven to move with the drum 40. Once engaged between the laying rollers 44 and the first sheet 1, the grippers 39 let go of the pieces 5 and are brought into the released position, interacting with the cams 91, and these pieces 5, held stretched as a result of the pressure force exerted by the rollers 44, are bonded to the first sheet 1 extending transversely relative to the direction of movement of the latter.

This first sheet 1, equipped with stretched pieces 5 of elastic band bonded transversely and uniformly spaced subsequently receives the longitudinal elastic bands 4. Then the absorbent wads 3 arranged between the transverse pieces 5 and finally the second non-woven sheet 2 which covers the various elastic members previously bonded and the absorbent wads 3 form the composite sheet N which is to be cut transversely at equal intervals approximately in the middle of each piece 5 of band, thus providing diapers.

Alternative Forms

Figure 15:
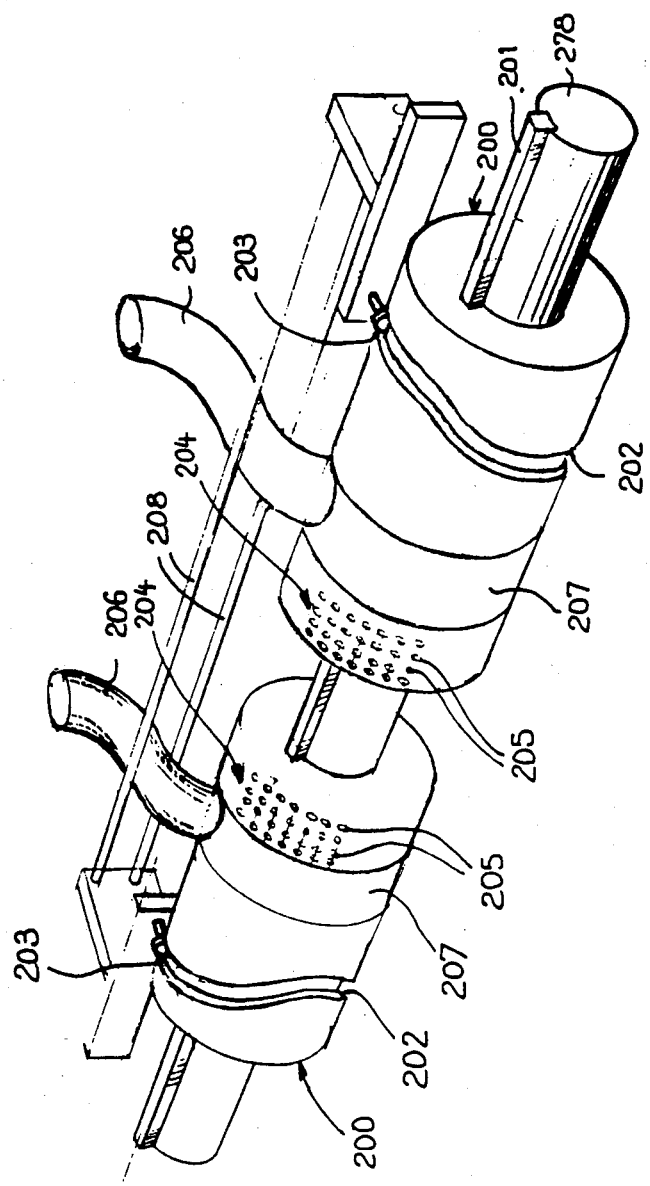

In rhe alternative embodiment of the stretching station illustrated in FIG. 15, the shaft 78 and the gripper devices retaining the pieces of band have been replaced by a shaft 278 which carries two cylindrical blocks 200 and on which the latter are mounted slideably, while at the same time being wedged in terms of rotation by means of a rib 201, along which they can slide.

Each block has near its end opposite the adjacent block a groove 202, which extends circumferentially over the outer periphery of the corresponding block 200.

Each groove delimits a sinusoidal period along the circumference of the respective block and interacts with a corresponding roller 203 integral with the frame.

The grooves 202 are approximately symmetrical relative to a plan perpendicular to the axis of the shaft 278 and form cams for controlling the sliding of the blocks on the shaft 278 in both directions during the rotation of the latter.

Each block 200 has in the region of its end adjacent to the other block a zone 204 of its cylindrical surface which is provided with perforations 205.

These two zones 204 have one and the same angular position relative to the shaft 278 and each extend angularly on the outer periphery of the corresponding block over a length at most equal to the width of the pieces 5 of band for a reason which will be explained below.

These perforated zones 204 each communicate with an aspirator (not shown) by means of a corresponding pipe 206 which opens out inside a respective bush 207 mounted movably in terms of rotation in a circumferential notch adjacent to the zone 204 of the corresponding block 200.

The interval arrangement of the blocks 200 and their associated bushes 207 is such that rotary joint is formed between each of these bushes 207 and the corresponding block 200 so that the partial vacuum supplied by the respective pipe 206 is transmitted to the perforations 205 of the corresponding zone 204.

To immobilize the pipes 206 relative to the blocks 200 and make it possible to guide them when these blocks slide axially on the shaft 278, these two pipes 206 pass between two bars 208 integral with the frame and parallel to the shaft 278. The rollers 203 are connected to these bars, being mounted rotatably about an axis perpendicular to the axis of rotation of this shaft 278.

The cylindrical shell delimited by these blocks 200 is approximately tangent to that delimited by the fingers 37 of the transfer station J and to that delimited by the drum 40 of the assembly station 7.

In this alternative form, the suction in the region of the zones 204 is synchronized with the operation of the transfer and assembly stations and with the movement of moving the blocks 200 axially away from one another and near to one another in such a way that, when these zones 204 come opposite a pair of fingers 37 carrying a piece 5 of band, these blocks 200 are in a position near to one another and in such a way that air is sucked through the perforations 205, thereby retaining each of the lateral ends of the pieces 5 of band on each of the zones 204.

During the rotation of the shaft 278 from the transfer station to the assembly station, the two blocks 200 move away from one another under the effect of the rollers 203 which interact in the cam grooves 202 so as to stretch the piece 5 of band carried by these blocks 200.

At the stage where this stretched piece of band is gripped between the first sheet and the laying rollers 44, the suction is cut off to free this piece and the blocks 200 continue to move in rotation up to the transfer station coming near to one another in order to grasp a new piece 5 of band there presented by a pair of fingers 37.

In combination with this alternative form, the drum 38 with fingers 37 of the transfer station J can be replaced by a conveyor belt which receives the pieces from the cutting station and deposits them in synchronism on the perforated zones of the blocks 200.

Many other alternative forms are, of course, possible without departing from the scope of the invention. Thus, the glue, instead of being deposited on the band 9, can be deposited downstream on the pieces 5 themselves or on the first sheet 1 in the region of the parts of its surface to which the pieces 5 of band are to be bonded.

It will be appreciated, moreover, that the number of knives 98, fingers 37 and grippers 39 is not limited to a particular value, the essential factor being that the various stations of the machine according to the invention are synchronized with one another.

I claim:

1. A machine for fastening stretched pieces of elastic band to a sheet driven in continuous movement comprising frame means, supply means for supplying pieces of band on said frame means, stretching means receiving said pieces of band and stretching said pieces of band, means for coating said pieces of band with an adhesive leaving uncoated sections of each band, means for laying and fastening said stretched and coated pieces of band on said sheet in the region of a bearing surface over which said sheet passes, and means synchronizing said supply means with said stretching means of synchronzied with the movement of said sheet, said stretching means being movably mounted in terms of rotation about a first axis transverse relative to the direction of movement of said sheet, said stretching means comprising respective means for retaining each lateral end of the pieces, means of shifting these respective retaining means relative to one another parallel to the first axis, said lateral ends being uncoated, said shifting means being of the cam type, said retaining means having grippers associated with actuating means synchronized with said laying and fastening means and with said supply means, each of the respective retaining means comprising gripper devices intended for retaining the corresponding uncoated lateral end of a piece of band, said gripper devices being distributed circumferentially around the first axis and each being located at the same angle and radial distance from this axis, each gripper device of each of the retaining means being arranged in one and the same angular position around the first axis as a corresponding associated device of the opposite retaining means, intended for retaining the opposite lateral end of the piece of band.

2. A machine according to claim 1, wherein each gripper is mounted pivotably on a respective support about an axis perpendicular to the first axis between an active position in which said gripper is capable of gripping the corresponding lateral end of a band between its active end and the corresponding support, and a released position, in which this active end of the gripper is away from the support, the actuating means comprising means for placing said gripper in the active position and means of releasing said gripper.

3. A machine according to claim 2, wherein said grippers have supports mounted slideably parallel to the first axis.

4. A machine according to claim 3, wherein there are two flanges spaced axially from one another on a shaft on which they are wedged in terms of rotation, said shaft extending according to the first axis and said gripper supports of each of the retaining means being carried by a respective flange and being mounted slideably between said two flanges.

5. A machine according to claim 4, wherein each gripper support is associated with a respective connecting rod, said connecting rod being articulated at each of its ends about axes parallel to one another, said connecting rod being connected at its ends to the corresponding support and one of said flanges.

6. A machine according to claim 5, wherein said shifting means comprises two cams integral with said frame means and spaced axially from one another between the two flanges, each of said cams extending circumferentially around said first axis.

7. A machine according to claim 6, wherein said connecting rods carried by each flange are equipped with a roller interacting with a corresponding cam taking the form of a groove, each roller being mounted movably in terms of rotation about a radial axis relative to said first axis, this radial axis being parallel to the axes of articulation of the respective connecting rod on each flange and on the corresponding support.

8. A machine according to claim 7, wherein said cams are formed on a sleeve through which the shaft passes, said sleeve being wedged on said frame means.

9. A machine according to claim 8, wherein said actuation means for putting each gripper in the active position comprises a respective elastic member arranged between said gripper and the corresponding support to stress the active end of said gripper in the direction of the respective support.

10. A machine according to claim 9, wherein said releasing means comprises two pairs of cams integral with said frame means, said grippers carried by each flange being associated with a respective pair of cams, each pair of cams comprising a first cam located in the vicinity of the supply means and a second cam located in the vicinity of the laying and fastening means, each gripper carrying a roller intended for interacting with the respective first and second cams.

11. A machine for fastening stretched pieces of elastic band to a sheet driven in continuous movement comprising frame means, supply means for supplying pieces of band on said frame means, stretching means receiving said pieces of band and stretching said pieces of band, means for coating said pieces of band with an adhesive leaving uncoated sections of each band, means for laying and fastening said stretched and coated pieces of band on said sheet in the region of a bearing surface over which said sheet passes, and means synchronizing said supply means with said stretching means and synchronized with the movement of said sheet, said stretching means being movably mounted in terms of rotation about a first axis transverse relative to the direction of movement of said sheet, said stretching means comprising respective means for retaining each lateral end of the pieces, means of shifting these respective retaining means relative to one another parallel to the first axis, said lateral ends being uncoated, said shifting means being of the cam type, said retaining means having grippers associated with actuating means synchronized with said laying and fastening means and with said supply means, each gripper extending parallel to the first axis, and the end of each gripper being oriented in the direction of the opposite associated gripper.

12. A machine for fastening stretched pieces of elastic band to a sheet driven in continuous movement comprising frame means, supply means for supplying pieces of band on said frame means, stretching means receiving said pieces of band and stretching said pieces of band, means for coating said pieces of band with an adhesive leaving uncoated sections of each band, means for laying and fastening said stretched and coated pieces of band on said sheet in the region of a bearing surface over which said sheet passes, and means synchronizing said supply means with said stretching means and synchronized with the movement of said sheet, said stretching means being movably mounted in terms of rotation about a first axis transverse relative to the direction of movement of said sheet, said stretching means comprising respective means for retaining each lateral end of the pieces, means of shfting these respective retaining means relative to one another parallel to the first axis, said lateral ends being uncoated, said retaining means being of the suction type.

13. A machine according to claim 12, including a cylindrical member forming an anvil, said sheet passing over said cylindrical member.

14. A machine according to claim 13, wherein said cylindrical member is a bell provided with perforations distributed over its cylindrical surface and said retaining means comprises a suction nozzle which is mounted on said frame means and is arranged inside said bell and extends opposite and near to at least part of the inner cylindrical surface of said bell.

* * * * *